US012618110B2

(12) United States Patent
Strom

(10) Patent No.: US 12,618,110 B2
(45) Date of Patent: May 5, 2026

(54) NUCLEIC ACID ANALYSIS USING EMULSION PCR

(71) Applicant: Quest Diagnostics Investments LLC, Secaucus, NJ (US)

(72) Inventor: Charles M. Strom, San Clemente, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 1238 days.

(21) Appl. No.: 17/486,700

(22) Filed: Sep. 27, 2021

(65) Prior Publication Data

US 2022/0010378 A1     Jan. 13, 2022

Related U.S. Application Data

(63) Continuation of application No. 15/455,491, filed on Mar. 10, 2017, now Pat. No. 11,130,997, which is a continuation of application No. 14/369,426, filed as application No. PCT/US2012/071758 on Dec. 27, 2012, now Pat. No. 9,593,375.

(60) Provisional application No. 61/582,200, filed on Dec. 30, 2011.

(51) Int. Cl.
| | |
|---|---|
| *C12Q 1/68* | (2018.01) |
| *C12Q 1/6851* | (2018.01) |
| *C12Q 1/6881* | (2018.01) |

(52) U.S. Cl.
CPC ......... *C12Q 1/6881* (2013.01); *C12Q 1/6851* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,548,255 | B2 | 4/2003 | Bensimon et al. |
| 6,610,186 | B1 | 8/2003 | Mayer et al. |
| 7,425,431 | B2 | 9/2008 | Church et al. |
| 7,875,432 | B2 | 1/2011 | Wu et al. |
| 9,593,375 | B2 * | 3/2017 | Strom ................. C12Q 1/6881 |
| 2010/0291658 | A1 | 11/2010 | Hollander et al. |
| 2011/0033854 | A1 | 2/2011 | Drmanac et al. |
| 2011/0159499 | A1 * | 6/2011 | Hindson .............. C12Q 1/6827 435/6.12 |
| 2011/0250597 | A1 | 10/2011 | Larson et al. |

FOREIGN PATENT DOCUMENTS

| | | |
|---|---|---|
| WO | WO-2011/100604 A2 | 8/2011 |

OTHER PUBLICATIONS

Advisory Action dated Nov. 6, 2019 in U.S. Appl. No. 15/455,491.
Extended European Search Report issued in application No. EP 18 20 2024 on Feb. 28, 2019 (9 pages).
Final Office Action dated Jul. 29, 2019 in U.S. Appl. No. 15/455,491.
Ge, Qinyu et al., "Emulsion PCR-based method to detect Y chromosome microdeletions," Analytical Biochemistry, Jul. 3, 2007, vol. 367, No. 2, pp. 173-178 (6 pages).
International Search Report dated Feb. 26, 2013 in PCT/US2012/071758.
Lebofsky et al., "Single DNA Molecule Analysis: Applications of Molecular Combing," Briefings in Functional Genomics and Proteomics, 2003, vol. 1, No. 4, pp. 383-396.
Michalet et al., "Dynamic Molecular Combing: Stretching the Whole Human Genome for High-Resolution Studies," Science, vol. 277, pp. 1518-1523, Jan. 1, 1997.
Notice of Allowance dated Oct. 28, 2016 in U.S. Appl. No. 14/369,426.
Notice of Allowance dated May 26, 2021 in U.S. Appl. No. 15/455,491.
Office Action dated Jan. 11, 2019 in U.S. Appl. No. 15/455,491.
Office Action dated Oct. 7, 2020 in U.S. Appl. No. 15/455,491.
Office Action dated Dec. 3, 2015 in U.S. Appl. No. 14/369,426.
Office Action dated Mar. 24, 2020 in U.S. Appl. No. 15/455,491.
Office Action issued Jul. 14, 2016 in U.S. Appl. No. 14/369,426.
Oshige et al., "A new DNA combing method for biochemical analysis," Analytical Biochemistry, vol. 400, pp. 145-147, May 1, 2010.
Supplementary European Search Report dated Jun. 24, 2015 in EP 12863794.
Zhong et al., "Multiplex digintal PCR: breaking the one target per color barrier of quantitative PCR," Lab on a Chip, vol. 11, No. 13, pp. 2167-2011, Jan. 1, 2011.

* cited by examiner

*Primary Examiner* — Stephanie K Mummert
(74) *Attorney, Agent, or Firm* — DUANE MORRIS LLP

(57) ABSTRACT

The present invention provides methods for analyzing large nucleic acids including chromosomes and chromosomal fragments. In one aspect, the present invention provides a method of nucleic acid analysis comprising the steps of (a) obtaining a sample of nucleic acid comprising at least one chromosome or fragment greater than about 1,000 base pairs in length and containing a target region; (b) creating an emulsion in which each drop of the emulsion contains an average of between about 0-2, 0-1.75, 0-1.5, 0-1.0, 0-0.75, 0-0.5, or fewer chromosomes or fragments of step (a), (c) performing emulsion PCR, (d) quantifying the number of emulsion droplets containing amplified nucleic acid from the target region; (e) calculating the ratio of droplets containing amplified nucleic acid from the target region to total droplets; and (f) comparing the ratio of step (e) to a reference ratio representing a known genotype.

18 Claims, No Drawings

NUCLEIC ACID ANALYSIS USING EMULSION PCR

CROSS REFERENCE TO RELATED APPLICATIONS

This application is a Continuation of U.S. application Ser. No. 15/455,491, filed Mar. 10, 2017, which is a Continuation of U.S. application Ser. No. 14/369,426, which is the U.S. National Stage of PCT/US2012/071758, filed Dec. 27, 2017, which claims the benefit under 35 U.S.C. § 119(e) of U.S. Provisional Application Ser. No. 61/582,200, filed Dec. 30, 2011, which is incorporated by reference in its entirety.

FIELD OF THE INVENTION

The present invention relates to methods of nucleic acid analysis, in particular methods using emulsion PCR in analysis of large nucleic acid fragments or whole chromosomes.

BACKGROUND OF THE INVENTION

The following discussion of the background of the invention is merely provided to aid the reader in understanding the invention and is not admitted to describe or constitute prior art to the present invention.

Many modern advances in cellular and molecular biology are rooted in the advent of large-scale amplification of nucleic acids and analytical methods dependent thereon. A number of methods are known in the art for performing such amplification of template nucleic acid molecules to generate populations of substantially identical copies. One technique that is particularly amenable to high throughput applications is emulsion polymerase chain reaction ("emulsion PCR" or "emPCR").

Emulsion PCR is performed by isolation of individual DNA molecules along with primer-coated beads in aqueous droplets within an oil phase. A PCR step coats each bead with clonal copies of the DNA molecule which are then immobilized for later sequencing. Emulsion PCR is used in a number of commercial methods, such as those of 454 Life Sciences, and SOLiD sequencing, (developed by Agencourt, now Applied Biosystems). Current emulsion PCR techniques involve the use of small fragments of DNA, which renders it unsuitable for analysis of certain genotypes such as those depending on an allelic linkage, and other applications for which assessment of large nucleic acids are required. Therefore, a need remains for emulsion PCR-based analytical methods that may applied to the evaluation of large nucleic acids including, for example, for monosomal analysis.

SUMMARY OF THE INVENTION

The present invention is based on the discovery that certain nucleic acid preparation techniques, such as those used in molecular combing, will facilitate the use of large nucleic acid fragments in emulsion PCR and subsequent analysis.

In one aspect, the present invention provides a method of nucleic acid analysis comprising the steps of (a) obtaining a sample of nucleic acid comprising at least one chromosome or fragment greater than about 1000 base pairs in length and containing a target region; (b) creating an emulsion in which each drop of the emulsion contains an average of between about 0-2, 0-1.75, 0-1.5, 0-1.0, 0-0.75, 0-0.5, or fewer chromosomes or fragments of step (a), (c) performing emulsion PCR, (d) quantifying the number of emulsion droplets containing amplified nucleic acid from the target region; (e) calculating the ratio of droplets containing amplified nucleic acid from the target region to total droplets; and (f) comparing the ratio of step (e) to a reference ratio representing a known genotype.

In another aspect, the present invention provides a method for determining the genotype of a subject (e.g., human) suspected to carry a 2+0 genotype comprising the steps of (a) obtaining a DNA sample comprising the locus of interest from the subject, (b) creating an emulsion in which each drop of the emulsion contains an average of between about 0-2, 0-1.75, 0-1.5, 0-1.0, 0-0.75, 0-0.5, or fewer chromosomes or fragments of step (a), (c) performing emulsion PCR, (d) quantifying the number of emulsion droplets containing amplified nucleic acid from the locus; (e) comparing the number of emulsion droplets from step (d) with the number of emulsion droplets containing amplified nucleic acid from the locus of a control 1+1 genotype sample, wherein a 1+1 genotypic sample will show successful amplification in about two times the emulsion droplets as the control and a negative sample with no successful amplification will indicate that the subject has a deletion of both alleles. In some embodiments, the locus of interest is the SMN1 gene on human chromosome 5.

A "2+0 genotype" of a diploid cell, as used herein, refers to a duplication of a genetic sequence on a chromosome with a deletion or other types of disruption of the sequence at the counterpart chromosome. The wild-type of a 2+0 genotype can be referred to as a "1+1 genotype" in which each chromosome of a pair contains a copy of the sequence. A 2+0 genotype can result from improper genetic recombination or translocation between the chromosomes, without limitation.

Since a 2+0 genotype and the corresponding 1+1 genotype have the same number of copies of the genetic sequence in a cell, they cannot be distinguished by dosage analysis (e.g., quantitative PCR with the entire cell) alone. The present disclosure, however, provides a ready solution. This is because the chromosome fragment enclosed in each emulsion drop is large enough to include both copies of the duplication in a 2+0 genotype, whereas, for a 1+1 genotype, the two copies that are located on separated on different chromosomes would be separated into different drops.

The methods of the present disclosure can also be used to improve sequencing efficiency experimentally and/or computationally. It is contemplated that the inclusion of a large (e.g., longer than 1000 basepairs, 10 kilobases (kb), 100 kb, 200 kb, 300 kb, 400 kb, 500 kb, 600 kb, 700 kb, 800 kb, 900 kb or 1,000 kb) intact fragment of a chromosome (a) enables subsequent sequencing of a relative longer sequence, and (b) facilitates sequence alignment among sequences obtained from within a drop since no sequence overlap is expected from sequencing a single copy of a genetic sequence.

In some embodiments, the nucleic acid of step (a) is processed by (i) obtaining a sample of nucleic acid in a solution (e.g., an aqueous solution); (ii) retracting the meniscus of the solution; and (iii) immobilizing the ends of the nucleic acid to facilitate isolation of the individual nucleic acid molecules. In some embodiments, the nucleic acids are immobilized by allowing the ends to bind to ionisable groups on a solid substrate (e.g., a silated glass plate). Immobilization preferably is performed at a pH below the pKa of the ionizable groups of the solution. In some embodiments, the rate of retraction of the meniscus is constant rate, and be about 300 µm/sec.

In other embodiments, the emulsion may be created by mechanical agitation or microfluidic droplet generation. The droplets may each be between about 15 and about 100 pL in volume. Further, the at least one chromosome or fragment may be greater than 10 kilobases (kb), greater than 100 kilobases (kb), greater than 200 kb, greater than 300 kb, greater than 400 kb, greater than 500 kb, greater than 600 kb, greater than 700 kb, greater than 800 kb, greater than 900 kb, greater than 1,000 kb or more in length. In further embodiments, the chromosome or fragment is between about 200 and about 700 kb in length.

As used herein, the term "stretching" refers to any process by which nucleic acid molecules in solution are elongated (i.e., unwound). In one embodiment, stretching is performed using the force of a receding meniscus to produces a high-density array of nucleic acid molecules. In other embodiments, the nucleic acids are at least about 10 kilobases (kb), 100 kb, 200 kb, 300 kb, 400 kb, 500 kb, 600 kb, 700 kb, 800 kb, 900 kb, 1,000 kb or more in length. In certain embodiments, the nucleic acids are between about 200 and 700 kilobases (kb) in length. In other embodiments, the nucleic acids subject to stretching are chromosomes or chromosome fragments.

As used herein, the term "emulsion drop" or "emulsion droplet" refers to any primer-coated aqueous droplet contained in an oil solution. The emulsion drop may be between about 15 and about 100 pL in volume, and may contain a nucleic acid template.

As used herein, the term "carrier state" is meant a person in which only one chromosome of a chromosome pair encodes a functional copy of the gene of interest. The copy of the gene of interest which is non-functional may be non-functional as a result of an inactivating mutation (i.e., the gene may be present but inactive) or may be partially or totally deleted from chromosome (e.g., resulting from a chromosomal deletion or translocation). In the case of the SMN1 gene located on chromosome 5, a carrier state occurs when one pair member of chromosome 5 lacks an SMN1 locus, but two copies of the gene are translocated onto the second pair member. This mutation produces little or no phenotypic effect when present in a heterozygous condition with a non-disease related allele, but produces a "disease state" when a person is homozygous, i.e., both pair members of chromosome 5 lack functional SMN1 nucleic acid sequences.

By "primer" is meant a sequence of nucleic acid, preferably DNA, that hybridizes to a substantially complementary target sequence and is recognized by DNA polymerase and serves as a substrate to initiate DNA replication in an amplification reaction (e.g., PCR).

As used herein, the term "substantially complementary" is meant that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, "amplification" is meant one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon."

As used herein, "biological sample" is meant a sample obtained from a biological source. When obtained from a subject (e.g., a human patient), a biological sample may, by way of non-limiting example, consist of or comprise blood, serum, plasma, cerebrospinal fluid (CSF), urine, feces, tissue samples including biopsy samples (e.g., obtained by a fine needle aspirate (FNA)), and those obtained by non-invasive techniques such as epidermal samples (e.g., cheek swabs), amniotic fluid, bone marrow sample and/or chorionic villi. The term biological sample includes samples which have been processed to release or otherwise make available a nucleic acid for detection as described herein. For example, a biological sample may include a cDNA that has been obtained by reverse transcription of RNA from cells in a biological sample.

By "anchoring" of the macromolecule on the surface, there should be understood an attachment resulting from a chemical reactivity both through a covalent linkage and a noncovalent linkage such as a linkage resulting from physicochemical interactions, such as adsorption.

DETAILED DESCRIPTION

The present invention is directed to the methods of nucleic acid analysis and, in particular, analysis of large nucleic acids using emulsion PCR techniques. The invention is particularly useful in situations wherein a genotype is characterized by an allelic linkage or lack thereof, and identification or diagnosis requires methods of analysis that keep the linkage intact. In the presently disclosed methods, whole chromosomes or large fragments are pretreated to facilitate their emulsion into droplets prior to undergoing emulsion PCR.

Nucleic Acid Preparation

As discussed below in greater detail, standard emulsion PCR is conducted using small nucleic acid fragments. In order to properly quantify many samples, however, it is imperative that larger fragments, or even whole chromosomes, be placed inside each droplet. In the present methods, the samples are therefore subjected to preparation steps prior to emulsion PCR to ensure that a large fragment size is maintained. In preferred methods, the preparation is similar to that undergone in molecular combing assay.

In molecular combing, deproteinized DNA molecules in solution with a random-coil conformation attach with non-sequence specificity to a silanized hydrophobic glass surface by their extremities. While not wishing to be bound by any theory, it is understood that pH-induced denaturation of the DNA ends exposes the hydrophobic domains of the bases, allowing a strong interaction with the hydrophobic surface. The glass surface is mechanically pulled out of the solution at a constant speed (300 µm/sec) where the receding air-water meniscus exerts a constant perpendicular force on the attached DNA molecules. This constant perpendicular force is central to obtaining uniformly stretched DNA of a singular orientation.

Other techniques can also result in the stretching and the alignment of molecules. A dynamic orientation of molecules in solution, anchored at one end, can be obtained by, for example, electrophoresis or by a hydraulic flow.

The force of the receding meniscus is insufficient to break either the DNA extremity-surface interaction or covalent bonds within the DNA molecule; however, the receding meniscus exerts sufficient force to overstretch DNA from its random-coil conformation to 150 percent of its molecular contour length. This degree of extension corresponds to a 65 pN applied force determined by DNA force/extension curves. Once in contact with air, the DNA sticks onto the surface preventing molecule retraction. DNA is most likely attached to the silanised surface at several closely spaced intervals, as determined by examining recoil following DNA photo-cleavage.

This anchorage of the macromolecule can be achieved directly on (or with) the surface, or indirectly, that is to say via a linkage such as another molecule, especially another molecule with biological activity. When the anchorage is achieved indirectly, the macromolecule can be grafted chemically on the said linkage, or can interact physico-chemically with the said linkage, in particular when the said intermediate linkage is a molecule with biological activity recognizing and interacting with the said macromolecule. Thus, in order to carry out the direct or indirect anchoring of the macromolecule on the surface, it is possible to use a solid surface having certain specificities. It is in particular possible to use certain pretreated surfaces which make it possible to attach certain proteins or DNA, whether modified or otherwise.

Suitable surfaces for anchoring large DNA fragments and/or chromosomes are commercially available (Covalink, Costar, Estapor, Bangs, Dynal for example) in various forms having at their surface COOH, NH2 or OH groups for example. It is, in this case, possible to functionalize the DNA with a reactive group, for example an amine, and carry out a reaction with these surfaces. However, these methods require specific functionalization of the DNA to be attached. A technique allowing anchorage without prior treatment of the DNA has also been described. This process consists in causing a free phosphate at the 5' end of the DNA molecule to react with a secondary amine of the surface (NH Covalink surface). Anchoring by adsorption can be achieved by adsorption of the end of the molecule by controlling the surface charge by means of the pH, the ionic content of the medium or the application of an electric voltage over the surface given the differences in adsorption between the ends of the molecule and its middle part. According to the present invention, nonfunctionalized DNA molecules were thus anchored, by way of example, on surfaces coated with molecules ending with a vinyl or amine group such as polylysine molecules, or various surfaces such as glass, coated with silane type molecules ending with vinyl or amine groups or alternatively glass cover slips previously cleaned in an acid bath. In this latter case, the surface of the glass indeed has SiOH groups.

In all these cases, the pH range where the DNA is anchored is chosen to be between a state of complete adsorption and an absence of adsorption, the latter being situated at a more basic pH. It is understood that this technique is very general and can be extended by persons skilled in the art to numerous types of surfaces. It is also possible to functionalize the DNA with a first reactive group or a protein with a first binding pair member in order to cause it to react with a surface coated with a second reactive group or with a second binding pair member which is capable of reacting specifically with each other. The binding pair members may be a pair of the type: biotin/streptavidin (Zimmermann and Cox) or digoxigenin/antibody directed against digoxigenin (anti-DIG) for example (Smith et al., Science 258, 1122 (1992)).

Preferably, the anchoring surfaces will have a low fluorescence level so as not to interfere with the detection of the molecules after their alignment, in particular if the detection is done by fluorescence. The support can therefore have a surface coated with a reactive group or with a molecule with biological activity. By "affinity", there should be understood here both a chemical reactivity and an adsorption of any type, this under optional conditions of attachment of the molecules onto the exposed group, modified or otherwise. In one embodiment, the surface is essentially compact, that is to say that it limits access by the macromolecule with biological activity to the inner layers and/or to the support, this in order to minimize nonspecific interactions. It is also possible to use surfaces coated with a reactive exposed group (for example $NH_2$, COOH, OH, CHO) or with a macromolecule with biological activity (for example: proteins, such as streptavidin or antibodies, nucleic acids such as oligonucleotides, lipids, poly-saccharides and derivatives thereof) which is capable of attaching an optionally modified part of the molecule. Thus, surfaces coated with streptavidin or with an antibody according to known processes ("Chemistry of Protein Conjugation and Cross-linking", S. C. Wong, CRC Press (1991)) are capable of attaching a macromolecule having, at a specific site, a biotin or an antigen. Likewise, surfaces treated so as to have single-stranded oligonucleotides can serve in order to anchor on them DNAs or RNAs having a complementary sequence.

Among the surfaces having an exposed reactive group, there may be mentioned those on which the exposed group is a —COOH, —CHO, $NH_2$, —OH group, or a vinyl group containing a double bond —CH—$CH_2$ which is used as it is or which can be activated so as to give especially —CHO, —COOH, —$NH_2$ or OH groups. The supports with highly specific surfaces according to the present invention can be obtained using various processes. There may be mentioned by way of example: (A) a layer of carbon-containing, optionally branched, polymer at least 1 nm thick, having reactive groups as defined above and (B) surfaces obtained by depositing or anchoring on a solid support one or more molecular layers; the latter can be obtained by forming successive layers attached through noncovalent linkages, as non-limiting example, Langmuir-Blodgett films, or by molecular self assembly, this allowing the formation of a layer attached by covalent linkage. In the first case, the surface can be obtained by polymerization of at least one monomer generating at the surface of the polymer the said exposed group, or alternatively by partial depolymerization of the surface of a polymer to generate the said exposed group, or alternatively by deposition of polymer. In this process, the polymer formed has vinyl linkages such as a polyene derivative, especially surfaces of the synthetic rubber type, such as polybutadiene, polyisoprene or natural rubber.

In the second case, the highly specific surface contains: on a support, a substantially monomolecular layer of an organic compound of elongated structure having at least: an attachment group having an affinity for the support, and an exposed group having no or little affinity for the said support and the said attachment group under attachment conditions, but optionally having, after chemical modification following the attachment, an affinity for one type of biological molecule. The attachment can first of all be of the noncovalent type, especially of the hydrophiliclhydrophilic and hydrophobic/hydrophobic type, as in Langmuir-Blodgett films (K. B. Blodgett, J. Am. Chem. Soc. 57, 1007 (1935). In this case, the exposed group or the attachment group will be either hydrophilic or hydrophobic, especially alkyl or haloalkyl groups such as $CH_3$, $CF_3$, $CHF_3$, $CH_2F$, the other group being hydrophilic. The attachment can also be of the covalent type, the attachment group will, in this case, react chemically with the support. Certain surfaces of similar structure have already been mentioned in the electronic field, especially when the attachments are covalent, L. Netzer and J. Sagiv, J. Am. Chem. Soc. 105, 674 (1983) and U.S. Pat. No. 4,539,061. Among the attachment groups, there must be mentioned more particularly the groups of the metal alkoxide or semiconductor type, for example silane, especially chlorosilane, silanol, methoxy- and ethoxysilane, silazane, as well as phosphate, hydroxyl, hydrazide, hydrazine, amine, amide, diazonium, pyridine, sulfate, sulfonic, carboxylic, boronic, halogen, acid halide, aldehyde groups.

The combing process produces a high-density array of DNA molecules that are between 200 and 700 kilobases (kb) in length. DNA fibers are uniformly stretched along their length regardless of sequence content. This uniform stretching provides a length scale relating physical distance on the surface to genomic length, i.e. 1 μm=2 kb. Typically, 50-100 diploid human genomes are combed onto 22×22 mm slides, making quantitative studies possible from the detection of multiple events per assay. For a complete discussion of molecular combing procedures, see, e.g., U.S. Pat. No. 6,548,255 to Bensimon et al., which is herein incorporated by reference in its entirety; see also Lebofsky and Bensimon, *Single DNA Molecule Analysis*, Briefings in Functional Genomics and Proteomics, Vol. 1, No. 4, 383-396 (2003).

Recovery and Dilution of Combed Nucleic Acid Products

The combed nucleic acids are then recovered. Recovery may be achieved by any means known in the art, such as, for example, the addition of a solution containing an agent, e.g., a restriction endonuclease or a component with a pH above the pKa of the ionized groups, that acts to release the anchor to the silated glass, or, in the alternative, recovery may be achieved physically by blotting the slide with NA-45 paper, washing it in TE buffer, heating in an elution buffer, and extracting using phenol and ethanol followed by centrifugation.

Emulsion PCR

The present methods utilize emulsion PCR for amplification of a monosome or fragment of interest. Typical embodiments of emulsion PCR methods include creating a stable emulsion of two immiscible liquids to create liquid (e.g., aqueous) droplets within which reactions may occur. In particular, the aqueous droplets of an emulsion amenable for use in PCR methods may include a first fluid, such as a water based fluid suspended or dispersed as droplets (also referred to as a discontinuous phase) within another fluid, such as a hydrophobic fluid (also referred to as a continuous phase) that typically includes an oil. Examples of oil that may be employed include, but are not limited to, mineral oils, silicone based oils, or fluorinated oils.

Optionally, in some embodiments, the emulsion may include one or more surfactants that act to stabilize the emulsion, which may be particularly useful for specific processing methods such as PCR. Some embodiments of surfactant may include one or more of a silicone or fluorinated surfactant. For example, one or more non-ionic surfactants may be employed that include, but are not limited to, sorbitan monooleate (also referred to as Span™ 80), polyoxyethylenesorbitan monooleate (also referred to as Tween™ 80), or in some preferred embodiments, dimethicone copolyol (also referred to as Abil® EM90), polysiloxane, polyalkyl polyether copolymer, polyglycerol esters, poloxamers, and PVP/hexadecane copolymers (also referred to as Unimer U-151), or in more preferred embodiments, a high molecular weight silicone polyether in cyclopentasiloxane (also referred to as DC 5225C available from Dow Corning).

The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agents may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate such as a bead for attachment of template and amplified copies of the template, amplified copies complementary to the template, or combination thereof. Further, the solid substrate may be enabled for attachment of other type of nucleic acids, reagents, labels, or other molecules of interest.

Embodiments of an emulsion useful with the presently described invention may include a very high density of droplets or microcapsules enabling the described chemical reactions to be performed in a massively parallel way. Additional examples of emulsions employed for amplification and their uses for sequencing applications are described in U.S. Pat. Nos. 7,638,276; 7,622,280; and U.S. patent application Ser. Nos. 10/767,899; and 11/045,678, each of which is hereby incorporated by reference herein in its entirety for all purposes.

Also embodiments sometimes referred to as UltraDeep Sequencing, generate target specific amplicons for sequencing may be employed with the presently described invention that include using sets of specific nucleic acid primers to amplify a selected target region or regions from a sample comprising the target nucleic acid. Further, the sample may include a population of nucleic acid molecules that are known or suspected to contain sequence variants comprising sequence composition associated with a research or diagnostic utility where the primers may be employed to amplify and provide insight into the distribution of sequence variants in the sample. For example, a method for identifying a sequence variant by specific amplification and sequencing of multiple alleles in a nucleic acid sample may be performed. The nucleic acid is first subjected to amplification by a pair of PCR primers designed to amplify a region surrounding the region of interest or segment common to the nucleic acid population. Each of the products of the PCR reaction (first amplicons) is subsequently further amplified individually in separate reaction vessels such as an emulsion based vessel described above. The resulting amplicons (referred to herein as second amplicons), each derived from one member of the first population of amplicons, are sequenced and the collection of sequences are used to determine an allelic frequency of one or more variants present. Importantly, the method does not require previous knowledge of the variants present and can typically identify variants present at <1% frequency in the population of nucleic acid molecules.

Some advantages of the described target specific amplification and sequencing methods include a higher level of sensitivity than previously achieved. Further, embodiments that employ high throughput sequencing instrumentation, such as for instance embodiments that employ what is referred to as a PicoTiterPlate® array (also sometimes referred to as a PTP™ plate or array) of wells provided by 454 Life Sciences Corporation, the described methods can be employed to generate sequence composition for over 100,000, over 300,000, over 500,000, or over 1,000,000 nucleic acid regions per run or experiment and may depend, at least in part, on user preferences such as lane configurations enabled by the use of gaskets, etc. Also, the described methods provide a sensitivity of detection of low abundance alleles which may represent 1% or less of the allelic variants. Another advantage of the methods includes generating data comprising the sequence of the analyzed region. Importantly, it is not necessary to have prior knowledge of the sequence of the locus being analyzed.

Applications

The present methods are broadly applicable, but are particularly useful in determining the genotype of a patient in cases wherein a genotype may be characterized by a linkage between two or more copies of a given locus. One example of such a genotype arises in the case of the SMN1 gene.

Spinal muscular atrophy (SMA), a disease characterized by the degeneration of the anterior horn cells of the spinal cord, causes symmetric proximal muscle weakness. In approximately 95% of cases, SMA is caused by the homozygous deletion of the survival motor neuron 1 (SMN1) gene (5q13) or its conversion to SMN2. The prevalence of SMA, an autosomal recessive disease, is approximately 1 in 10,000 newborns. The carrier frequency of SMN mutation has been reported to be different among different ethnic groups in North America: the carrier frequency was measured to be 2.7% in Caucasians, 1.8% in Asians, 1.1% in African Americans, and 0.8% in Hispanics. The carrier frequency of the latter 2 groups was lower than that of the former groups. Determination of the copy number of the SMN gene is important for detecting spinal muscular atrophy (SMA) carriers and compound heterozygous patients. Copy number analysis of the SMN1 gene is important to identify carriers with SMN mutation. The American College of Medical Genetics (ACMG) recommends universal screening for the presence of SMA mutation to identify carriers because this condition is associated with clinically severe presentation and a high carrier frequency. Since SMA occurs in all populations, regardless of race or ethnicity, carrier testing is often recommended to couples considering pregnancy or in early stages of pregnancy. For a complete discussion of the effects of SMN1 copy number on SMA prevalence, see, e.g., Yoon et al., *Determination of SMN1 and SMN2 Copy Numbers in a Korean Population using Multiplex Ligation-dependent Probe Amplification*, Korean J Lab Med; Vol. 30:93-6, 2010, which is hereby incorporated by reference in its entirety.

By SMN gene dosage analyses to identify SMA carriers with only one copy of SMN1, three copies of SMN1 have been identified in normal individuals, implying the presence of two copies of SMN1 on a single chromosome 5. The presence of this '2-copy-SMN1 allele' is associated with a decreased SMN2 copy number. Importantly, SMA carriers may have two copies of SMN1 on one chromosome 5 and a deletion/conversion mutation of SMN1 on the other chromosome 5 (the '2+0' SMN1 genotype). By dosage analysis alone, such carriers, as well as carriers of small, intragenic mutations, are indistinguishable from normal individuals with one copy of SMN1 on each chromosome 5, unless a monosomal analysis technique is utilized. See, e.g., Ogino et al., *New insights on the evolution of the SMN1 and SMN2 region: simulation and meta-analysis for allele and haplotype frequency calculations*, European Journal of Human Genetics Vol. 12, 1015-1023, 2004.

The following examples serve to illustrate the present invention. These examples are in no way intended to limit the scope of the invention

EXAMPLES

The present methods will be understood more readily by reference to the following examples, which are provided by way of illustration and are not intended to be limiting.

Example 1: Identification of Subjects Carrying a 2+0 Genotype of SMN1

A blood sample is obtained from a patient. DNA is extracted from the sample using a 25:24:1 phenol/chloroform/isoamyl alcohol mixture and 10 seconds of vortex followed by 15 seconds of microcentrifuge. 3 M sodium acetate is added to the DNA solution, followed by precipitation using 100% cold ethanol. The solution is microcentrifuged for five minutes, and the supernatant removed. The resulting pellet of intact DNA chromosomes is dried and resuspended in buffer. The DNA is then placed into a solution in the reservoir of a genetic combing system (Genomic Vision®) with a silated glass cover slip, which, after an incubation period, is removed at a steady speed of 300 μm/sec. The stretched DNA is recovered by rinsing with a solution in which the pH is lower than the pKa of the ionized groups at the ends of the stretched chromosomes, followed by precipitation and removal of the excess solution.

Polymerase chain reaction (PCR) primer pairs are designed using the SMN1 gene sequences in EMBL/Genbank (Accession Nos. NM_000344.3, NM_022874.2. Each PCR primer for the PCR reactions contains either a forward linker sequence or a reverse linker sequence as appropriate to allow universal sequence reaction priming. DNA samples and primers and probes are combined with the QuantaLife Master Mix™ to create eight samples of 20 μL each, which are subsequently loaded into an eight-well droplet generator cartridge. The cartridge is loaded into a droplet generator which creates an emulsion of approximately 20,000 monodisperse droplets for each sample, each containing an average of 1 chromosome.

Emulsified samples are pipetted into a conventional 96-well PCR plate and amplified over 40 cycles at 97° C. for 30 seconds using a standard thermal cycler. Results are read using QuantaLife™ software, and droplets positive and negative for SMN1 are quantified. The positive to negative amplification ratios are compared to the ratios determined in Example 2, below, and correlated to a genotype.

Example 2: Determination of Ratios for Diagnosis

To confirm that 1+1 genotype samples will show successful amplification in approximately twice as many emulsion droplets as 2+0 genotype samples, a biological sample obtained from a subject with the 2+0 genotype and containing the SMN1 locus undergoes restriction enzyme digestion in one aliquot prior to emulsion PCR per the protocol described above in Example 1. The restriction enzyme splits the allelic linkage found in the 2+0 genotype, such that when the sample undergoes emulsion PCR, each copy of SMN1 is separated into a distinct emulsion droplet. PCR and quantification of positive and negative droplets will reveal that successful amplification occurs twice as often in the restriction enzyme-digested sample.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

I claim:

1. A method for determining the genotype of a subject suspected to carry a 2+0 genotype comprising:
   (a) creating an emulsion from an aqueous nucleic acid sample comprising a locus of interest on at least one stretched chromosome or a fragment thereof, wherein each emulsion droplet contains an average of between 0-2 nucleic acids from the aqueous nucleic acid sample;
   (b) amplifying the locus of interest within the emulsion;
   (c) quantifying the number of emulsion droplets that comprise an amplified locus of interest; and
   (d) calculating the ratio of droplets containing the amplified locus of interest to the total droplets and identifying the subject (i) as having a 2+0 genotype; (ii) as having a 1+1 genotype; or (iii) having a homozygous deletion.

2. The method of claim 1, wherein the subject has a 2+0 genotype when the number of emulsion droplets that comprise the amplified locus of interest is less than two times the number of droplets amplified from a sample known to have a 1+1 genotype.

3. The method of claim 1, wherein the subject has a 1+1 genotype when the number of emulsion droplets that comprise the amplified locus of interest is greater than two times of the number of droplets amplified from a sample known to have 1+1 genotype.

4. The method of claim 1, wherein the subject has a homozygous deletion of the locus of interest when there are no droplets comprising an amplified locus of interest.

5. The method of claim 1, wherein the aqueous nucleic acid sample is prepared by
   (i) retracting the meniscus of a solution of nucleic acid at a constant rate;
   (ii) anchoring the ends of the nucleic acid to a solid substrate; and
   (iii) recovering the nucleic acid from the solid substrate following steps (i) and (ii).

6. The method of claim 1, wherein the emulsion is created by mechanical agitation or microfluidic droplet generation.

7. The method of claim 1, wherein the emulsion droplets generated are each between about 15 and about 100 pL in volume.

8. The method of claim 1, wherein the fragment is greater than 10 kilobases (kb), greater than 100 kb, greater than 200 kb, greater than 300 kb, greater than 400 kb, greater than 500 kb, greater than 600 kb, greater than 700 kb, greater than 800 kb, greater than 900 kb, greater than 1,000 kb or more in length.

9. The method of claim 8, wherein the fragment is between about 200 and about 700 kb in length.

10. The method of claim 1, wherein the locus of interest is a SMN1 locus.

11. The method of claim 1, wherein the emulsion further comprises oligonucleotide primers for amplification of the locus of interest.

12. The method of claim 1, wherein the emulsion droplets are within an oil phase.

13. The method of claim 12, wherein the oil phase comprises a mineral oil, a silicone based oil, or a fluorinated oil.

14. The method of claim 1, wherein the emulsion further comprises a surfactant.

15. The method of claim 14, wherein the surfactant is a non-ionic surfactant.

16. The method of claim 15, wherein the surfactant is cyclopentasiloxane, dimethicone copolyol, polysiloxane, polyalkyl polyether copolymer, polyglycerol ester, poloxamer, PVP/hexadecane copolymer, sorbitan monooleate, or polyoxyethylenesorbitan monooleate.

17. The method of claim 1, wherein the at least one chromosome or a fragment thereof has been stretched lengthwise to about 150 percent of its molecular contour length.

18. The method of claim 1, wherein each emulsion droplet contains an average of between 0-0.75 nucleic acids from the aqueous nucleic acid sample.

* * * * *